(12) United States Patent
Haenggi et al.

(10) Patent No.: US 9,089,647 B2
(45) Date of Patent: Jul. 28, 2015

(54) APPARATUSES, SYSTEMS, AND METHODS FOR FILLING A CONTAINER WITH A LIQUID DRUG

(75) Inventors: Roger Haenggi, Nunningen (CH); Urs Rindlisbacher, Thoerishaus (CH); Franco Moia, Frenkendorf (CH); Marcel Mueller, Therwil (CH); Christoph Huwiler, Arth (CH); Florian Kuhni, Rohrbach (CH); Joerg Wermelinger, Schaffhausen (CH); Andreas Lischewski, Loehningen (CH); Christian Classen, Tengen (CH); Tilo Callenbach, Muri (CH); Louis Widmer, Ulisbach (CH); Maurice Ducret, Burgdorf (CH)

(73) Assignee: Roche Diagnostics International AG, Rotkreuz (CH)

( * ) Notice: Subject to any disclaimer, the term of this patent is extended or adjusted under 35 U.S.C. 154(b) by 0 days.

(21) Appl. No.: 13/492,008

(22) Filed: Jun. 8, 2012

(65) Prior Publication Data

US 2013/0035658 A1    Feb. 7, 2013

Related U.S. Application Data

(63) Continuation of application No. PCT/EP2010/007423, filed on Dec. 7, 2010.

(30) Foreign Application Priority Data

Dec. 9, 2009    (EP) .................................... 09405222

(51) Int. Cl.
*A61B 19/00* (2006.01)
*A61M 5/24* (2006.01)

(52) U.S. Cl.
CPC ....................................... *A61M 5/24* (2013.01)

(58) Field of Classification Search
CPC . A61J 1/2096; A61J 1/2089; A61J 2001/201; A61J 2001/2013; A61M 2209/045
USPC ...................... 604/361, 403–408; 53/467–473
See application file for complete search history.

(56) References Cited

U.S. PATENT DOCUMENTS 3,809,298 A * 5/1974 Harris et al. .................. 222/386
3,831,602 A * 8/1974 Broadwin ..................... 604/210
(Continued)

FOREIGN PATENT DOCUMENTS

EP    1820485 A1    2/2006
EP    1779830    *    5/2007
(Continued)

OTHER PUBLICATIONS

National Institutes of Health, Patient Information Publications: Giving a Subcutaneous Injection (2002). Previously located at http://www.cc.nih.gov/ccc/patient_education/pepubs/subq.pdf and mapped back to 2004 via the Wayback Machine.*
(Continued)

*Primary Examiner* — Philip R Wiest
*Assistant Examiner* — Ariana Zimbouski
(74) *Attorney, Agent, or Firm* — Dinsmore & Shohl LLP

(57) ABSTRACT

In one embodiment, a method of filling a container with a liquid drug from a drug reservoir may include: a) connecting a container and a drug reservoir with a cannula such that the drug reservoir and the container fluidically communicate with each other via the cannula, while being hermetically sealed; b) reducing a first volume contained within the container to displace a gaseous medium from the first volume of the container via the cannula into a second volume contained within the drug reservoir; c) increasing the first volume of the container to displace the liquid drug from the second volume of the drug reservoir into the first volume of the container to fill the container; and d) disconnecting the container and the drug reservoir. Before performing action d), action b) and action c) can be successively performed more than once to stepwise increase an amount of liquid drug displaced.

19 Claims, 11 Drawing Sheets

(56) References Cited

U.S. PATENT DOCUMENTS

| | | | |
|---|---|---|---|
| 4,883,101 A | 11/1989 | Strong | |
| 8,065,913 B2 * | 11/2011 | McCracken et al. | 73/304 R |
| 8,231,596 B2 * | 7/2012 | Okiyama | 604/408 |
| 8,257,336 B2 * | 9/2012 | Zihlmann | 604/403 |
| 2002/0189712 A1 | 12/2002 | Safabash | |
| 2002/0193738 A1 * | 12/2002 | Adzich et al. | 604/113 |
| 2003/0105430 A1 | 6/2003 | Lavi et al. | |
| 2005/0146323 A1 * | 7/2005 | Kleinen et al. | 324/207.26 |
| 2006/0169348 A1 * | 8/2006 | Yigal | 141/21 |
| 2008/0190988 A1 * | 8/2008 | Pedicini et al. | 227/130 |

FOREIGN PATENT DOCUMENTS

| | | |
|---|---|---|
| EP | 1779830 A1 | 5/2007 |
| WO | 2005084734 A1 | 9/2005 |
| WO | 2009014955 A2 | 1/2009 |

OTHER PUBLICATIONS

International Search Report mailed Jun. 16, 2011 pertaining to PCT/EP2010/007423.

* cited by examiner

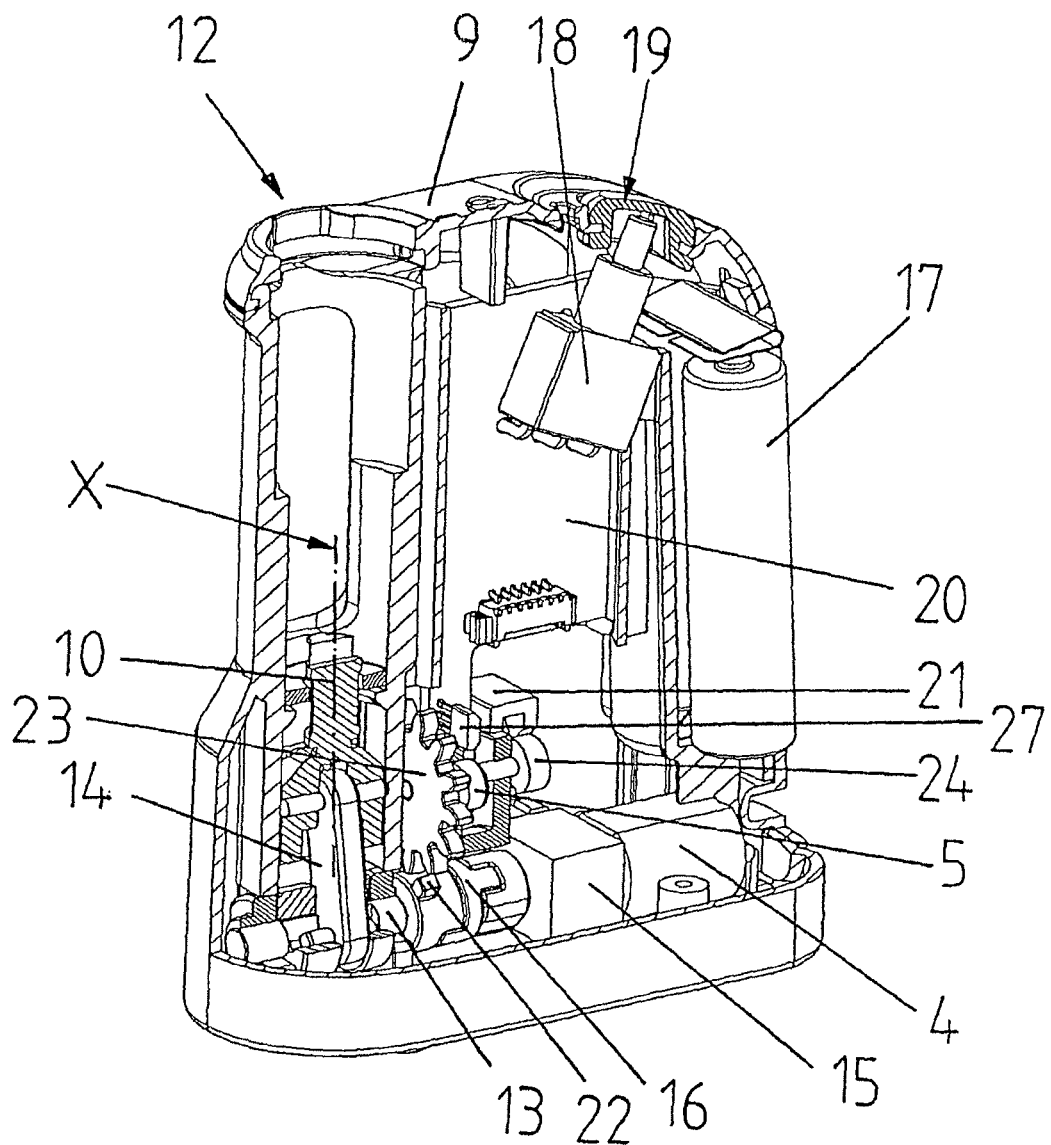

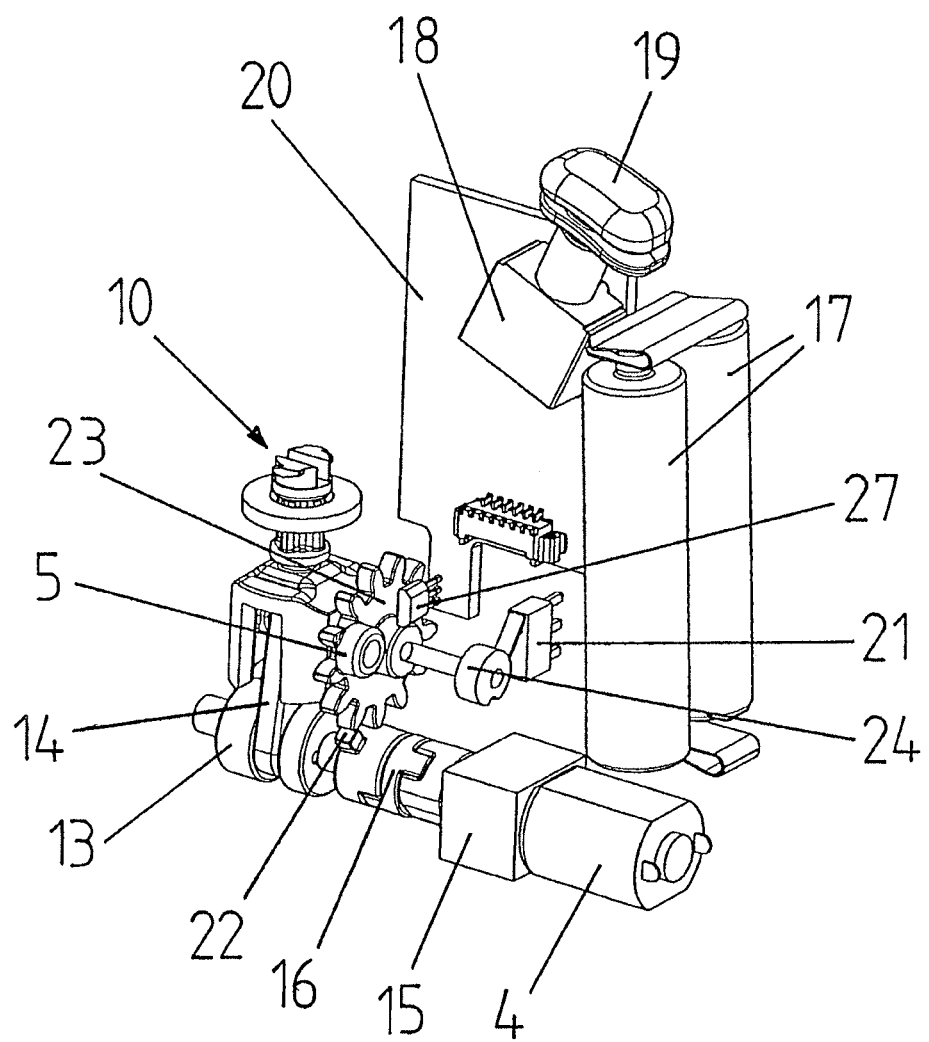

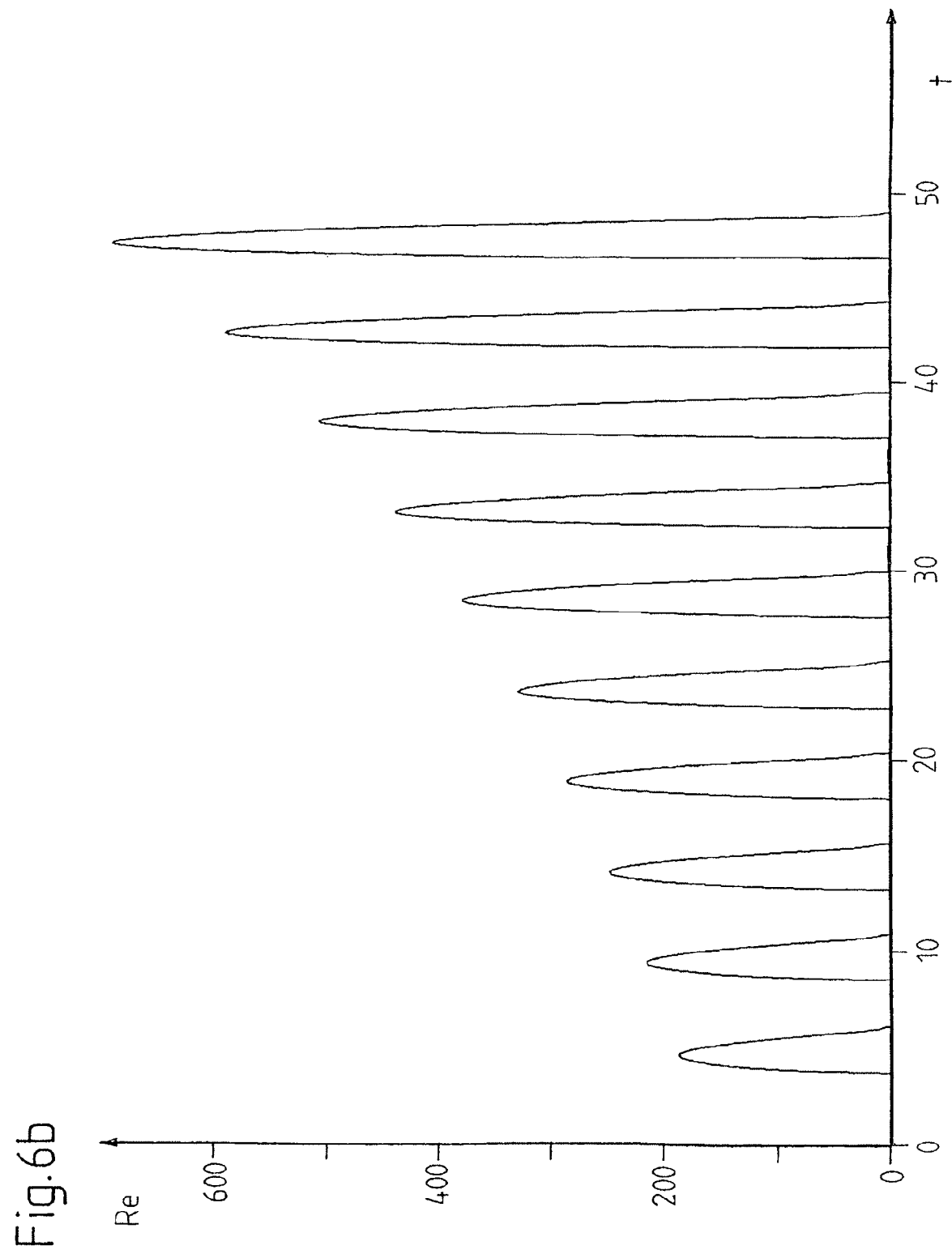

APPARATUSES, SYSTEMS, AND METHODS FOR FILLING A CONTAINER WITH A LIQUID DRUG

CROSS REFERENCE TO RELATED APPLICATIONS

This application is a continuation of International Application No. PCT/EP2010/007423 filed Dec. 7, 2010, which claims priority to EP 09 405 222.2 filed on Dec. 9, 2009. The contents of each of these applications are hereby incorporated by reference in their entirety into this disclosure.

TECHNICAL FIELD

The embodiments of the present disclosure relate generally to filling apparatuses, systems, and methods thereof, to methods of filling containers with a liquid drug from a drug reservoir, to apparatuses for use in a method of filling a container with a liquid drug from a drug reservoir, and to systems for extracting a liquid drug from a drug reservoir.

BACKGROUND

In the medical field, liquid drugs, such as insulin, can be supplied from a reservoir container that contains an amount of the liquid drug. The liquid drug can be transferred from the reservoir container to a container that receives a single dose of the drug, or an amount of the drug, which is suitable for a limited time of therapy of a patient. For example, doctors and nurses can draw medications from vials into syringes in order to inject the medications into patients. Patients can also inject themselves in a similar manner. For example, diabetes can be treated with the use of an insulin pump that supplies insulin from insulin ampoules. The insulin ampoules can be purchased without being filled with medication, i.e., as empty ampoules. Accordingly, patients may fill the empty ampoules from a vial containing an amount of insulin prior to use.

Some of the patients that fill the empty ampoules may suffer from movement disorders due to their disease and/or age. Thus, some patients may have difficulties in safely handling standard syringe assemblies or the like. Filling systems have been developed to assist with the process of filling ampoules from vials.

One example system is shown and described in EP 1 820 485 A1. The system provides a number of empty, single use ampoules made of plastic. Each of the ampoules can be formed by a container and a piston arranged therein in displaceable manner. A multi use piston rod can have a thread arranged at one end of the piston rod that is coupled to the piston of the ampoules. At the end of the ampoule facing away from the end of the ampoule where the piston rod can be coupled to the piston, each ampoule can include a connector with a cannula. The ampoule can be connected to a commercially available vial in via the connector such that the ampoule and the vial fluidically communicate with each other via the cannula, while the ampoule and the vial are structurally connected with each other.

One of the ampoules can be filled with insulin from a vial. Specifically, the piston rod is connected with the piston of the ampoule by screwing it with its threaded end into a corresponding thread formed in the piston. After that, the piston is pulled back with the piston rod, which can cause the inside of the ampoule is filled with air. The ampoule can then be coupled with the connector facing downwards to a vial. Next, the piston can be pushed into the container of the ampoule with the piston rod in order to displace the air contained inside the ampoule into the vial, and create an overpressure in the vial. In this state, the assembly can be turned upside down such that the vial is now on top. Then, the piston rod can be released. The overpressure in the vial can cause insulin to flow through the connector into the ampoule, and the piston to be displaced. Once the overpressure has dissipated, the displacement of the piston is stopped. The piston can be displaced until it reaches its original position via the piston rod to draw additional insulin into the ampoule. In this state the vial, the connector and the piston rod can be removed from the ampoule, which leaves the ampoule full of insulin and ready for use.

Accordingly, the example system can be utilized for filling ampoules from vials without needles. Thus, the risk of accidental needle sticks can be reduced compared filling a syringe arrangement. However, proper use of the system is required to avoid formation of foam and air bubbles within the ampoule. Furthermore, when the ampoule is filled with insulin from a smaller pen cartridge instead of from a vial, there is the risk that insulin may be spilled. Specifically, when the piston is fully pushed into the container of the ampoule with the piston rod, a piston of the pen cartridge can be pushed out of the cartridge causing the insulin contained therein to be spilled.

Another example of an ampoule filling system having similar functionality and shortcomings is disclosed in US 2002/0189712 A1.

Accordingly, additional methods, apparatuses and systems for filling containers with liquid drugs are needed.

SUMMARY

It is against the above background that the present disclosure is provided.

In one embodiment, a method of filling a container with a liquid drug from a drug reservoir may include: a) connecting the container and the drug reservoir with a cannula such that the drug reservoir and the container fluidically communicate with each other via the cannula, while being hermetically sealed; b) reducing a first volume contained within the container to displace a gaseous medium from the first volume of the container via the cannula into a second volume contained within the drug reservoir; c) increasing the first volume of the container to displace the liquid drug from the second volume of the drug reservoir into the first volume of the container to fill the container; and d) disconnecting the container and the drug reservoir. Before performing action d), action b) and action c) can be successively performed more than once to stepwise increase an amount of liquid drug displaced to the first volume of the container.

In another embodiment, an apparatus for filling an ampoule with a drug from a reservoir may include a housing, a piston rod, and a drive. The ampoule can be formed by a container and may include a piston arranged therein in a displaceable manner. The piston rod that can be moveable relative to the housing along a longitudinal axis of the piston rod. The piston rod may include a coupling member. When the coupling member couples the piston rod to the piston of the ampoule, a positive locking or a non-positive locking can occur between the piston rod and the piston along both directions of the longitudinal axis. The drive can actuate the piston rod along the longitudinal axis. Upon activation of the drive, the piston rod can be actuated back and forth along the longitudinal axis several times.

In yet another embodiment, an apparatus for filling an ampoule with a liquid drug from a drug reservoir may include a housing, a piston rod, a holding member, and a drive. The ampoule can be formed by a container and may include a piston arranged therein in displaceable manner. The piston rod that can be fixed with respect to the housing. The piston rod may include a coupling member. When the coupling member of the piston rod is coupled to the piston of the ampoule, a positive locking or a non-positive locking can occur between the piston rod and the piston in both directions of a longitudinal axis. When the coupling member couples the piston rod to the piston of the ampoule, the coupling member can hold the container of the ampoule such that the holding member is moveable relative to the piston rod along the longitudinal axis of the piston rod. The drive can move the holding member along the longitudinal axis of the piston rod. At least while the drive is activated, a positive locking and/or frictional locking can be made between the container of the ampoule and the holding member in both directions of the longitudinal axis of the piston rod. Upon being activated, the drive can actuate the holding member back and forth along the longitudinal axis of the piston rod several times.

In a further embodiment, a system for extracting a liquid drug from a drug reservoir may include an ampoule, a drug reservoir, a cannula, and a drive. The ampoule can be formed by a container. The ampoule may include a piston arranged therein in a displaceable manner. The container and the piston can bound a changeable volume of the ampoule. The drug reservoir can be hermetically sealed to the ampoule. The drug reservoir can contain an interior volume having a liquid drug contained therein. The cannula can be in fluidic communication with the changeable volume of the ampoule and the interior volume of the drug reservoir. The drive can cause relative motion along a longitudinal axis between the container and the piston of the ampoule. The drive can be actuated to: a) reduce the changeable volume of the ampoule such that a gaseous medium is displaced from the changeable volume into the interior volume of the drug reservoir; and b) increase the changeable volume of the ampoule such that the liquid drug is displaced from the interior volume of the drug reservoir into the changeable volume of the ampoule. Action a) and action b) can be successively performed more than once to stepwise increase an amount of liquid drug displaced to the changeable volume of the ampoule.

These and other features and advantages of the present disclosure will be more fully understood from the following detailed description taken together with the accompanying claims.

BRIEF DESCRIPTION OF THE DRAWINGS

The following detailed description of the embodiments of the present disclosure can be best understood when read in conjunction with the following drawings, where like structure is indicated with like reference numerals and in which:

FIGS. 4a to 4c schematically depict an apparatus according to one or more embodiments shown and described herein;

FIG. 6b graphically depicts system pressures and the Reynolds number in the cannula during performance of methods according to one or more embodiments shown and described herein using an embodiment of the apparatus schematically depicted in FIGS. 5a to 5b.

DETAILED DESCRIPTION

Figure 1:
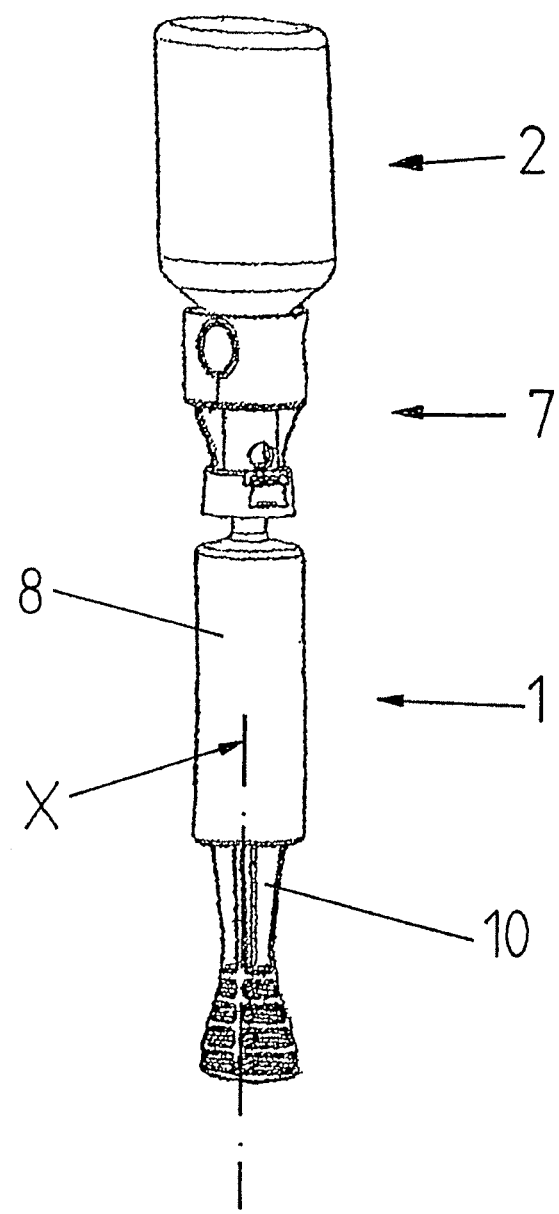
FIG. 1 schematically depicts a side view of an ampoule filling system according to one or more embodiments shown and described herein.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 7:
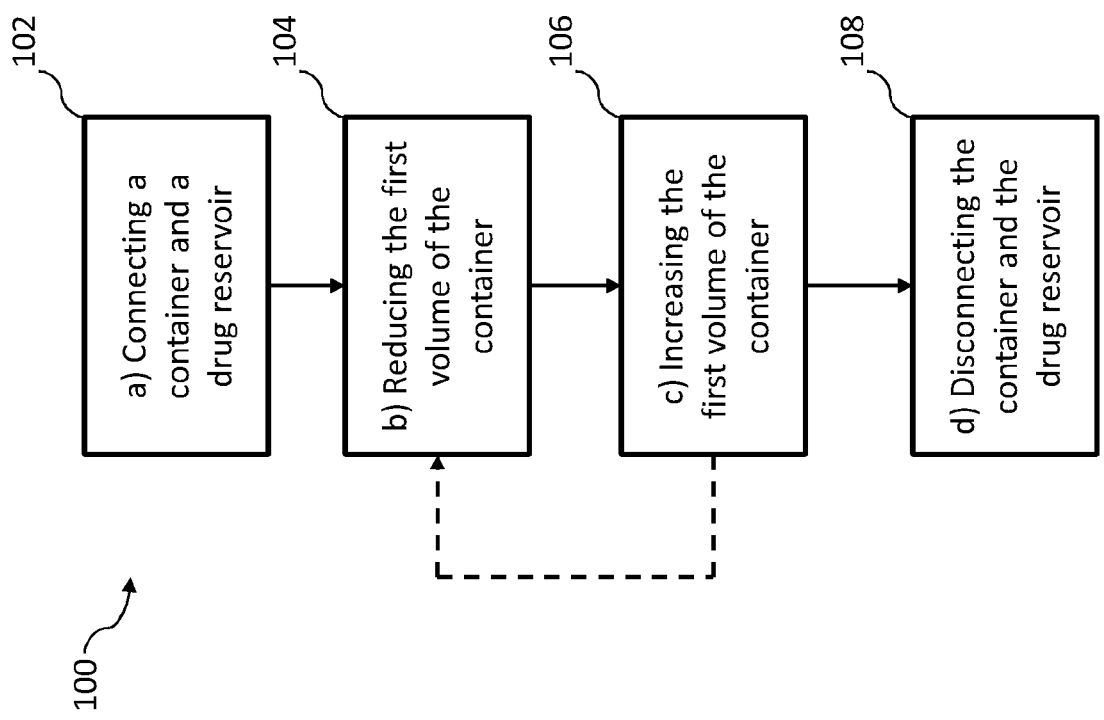
FIG. 7 schematically depicts a method according to one or more embodiments shown and described herein.

According to the embodiments described herein, methods for filling a container with a liquid drug, like e.g. a liquid painkiller or insulin, from a drug reservoir are provided. Referring now to FIG. 7, in at least one exemplary embodiment, a method 100 may include one or more of the following actions:

At process 102, the following action can be performed—a) connecting the container and the drug reservoir with a cannula such that the inside of the drug reservoir and the inside of the container fluidically communicate with each other via a cannula, while being hermetically sealed against the outside;

At process 104, the following action can be performed—b) reducing the volume of the inside of the container, thereby displacing a gaseous medium from the inside of the container via the cannula into the inside of the drug reservoir;

At process 106, the following action can be performed—c) increasing the volume of the inside of the container, thereby displacing liquid drug from the inside of the drug reservoir into the inside of the container for filling the container; and At process 108, the following action can be performed—d) disconnecting the filled container and the liquid drug reservoir.

According to at least one embodiment of the method for filling a container of the present disclosure, actions b) and c) can be successively performed more than once before action (generally indicated in FIG. 7 by dashed arrow line) d) is performed. Accordingly, in at least one embodiment the amount of liquid drug contained inside the container can be increased stepwise before the container and the liquid drug reservoir are disconnected.

It is noted that, the maximum pressure inside the liquid drug reservoir can be reduced significantly during the filling process of the container. Thus, the risk of formation of foam and/or air bubbles within the liquid drug that is filled into the container can be reduced. Furthermore, when the liquid drug reservoir is a pen cartridge, the risk that the piston of the pen cartridge will be pushed out of the cartridge, which can lead to the liquid drug contained therein being spilled, can be reduced.

The container that is filled, according to at least one embodiment of the present disclosure, can be at least one of a syringe type container, an ampoule, or a bag type container. Syringe type containers may be formed from a substantially rigid container body having a piston arranged therein in displaceable manner, which defines a changeable volume. The volume contained within the container can be altered through displacing the piston. An ampoule can be a syringe type container that, for example, has a septum or a Luer-type connector, at a front face. A bag type container can have a collapsible container body and connectors for establishing fluidic communication to the interior of the container. While the container types described herein are suitable for use the methods of the present disclosure, it is noted that additional container types can find favorable utility with the embodiments described herein.

According to the embodiments of the methods described herein, actions b) and c) can be successively performed at least three times before performing action d) such as, for example, at least five times in one embodiment, at least eight times in another embodiment or at least ten times in yet another embodiment. Accordingly, the container can be filled in several small steps, which may further reduce the risk of foam and/or air bubble formation within the liquid drug transferred to the container. Moreover, the maximum pressure in the liquid drug reservoir can be kept below critical values, especially for pen cartridges, which can reduce the risk of both foam and/or air bubble formation and the piston being pushed out from the pen cartridge.

In at least one embodiment of the present disclosure, the full capacity of the container can be filled. For example, in one exemplary method actions b) and c) can be successively performed until the container is substantially filled with the liquid drug, i.e., until the container contains a design capacity of liquid drug.

In one embodiment of the method, action d) can be performed with a container having an inside volume that is about equal to the inside volume it had when action b) was commenced for the first time. Accordingly, when filling an ampoule, an empty ampoule can initially be connected to the liquid drug reservoir with a piston of the ampoule in a desired position. The filled ampoule can be disconnected from the liquid drug reservoir with the piston positioned in substantially the same position within the container body.

In at least one embodiment of the method, before action c) is performed for the first time, action b) can be performed or before action b) is performed for the first time, action c) can be performed. Further, in some embodiments, the respective order of actions b) and c) can depend upon the total pressure level in the filling system.

The volume of the inside of the container can in at least one embodiment be reduced in action b) incrementally from the maximum volume in several small steps. For example, the reduction may be less than one half of the maximum volume of the inside of the container, less than one fourth of the maximum volume of the inside of the container or less than one tenth of the maximum volume of the inside of the container. Accordingly, several small filling steps can result when filling the container until it contains its design volume of liquid drug.

The inside of the container can in at least one embodiment be increased in action c) proceeding action b) in an amount that is substantially identical to the reduction in volume of action b). Accordingly, the pressure increase generated inside the filling system when performing action b) can be subsequently revoked in action c). Thus, a stepwise increase of the pressure in the system can be avoided. As is noted above, when the liquid drug reservoir is provided as a pen cartridge, a stepwise increase in filling system pressure can cause the piston of a pen cartridge to be pushed out of the cartridge and the liquid drug contained therein to be spilled.

In further embodiments of the method of the present disclosure, action b) can be performed more rapidly than action c) that immediately proceeds and/or precedes the action b). Alternatively, action c) can be performed more rapidly than action b) that immediately precedes the action c). The type of liquid drug, type of container to be filled and the dimensions of the filing system can have an impact on the relative speed of actions b) and c). Specifically, a relatively fast action b) may be preferable with regard to a short filling time, while a relatively fast action c) may be preferable with regard to prevention of foam or bubble formation.

In at least one embodiment of the present disclosure, the speed of the increase in volume of the inside of the container in action c) is substantially constant. Accordingly, peaks in the flow velocity of the flow of liquid drug through the cannula can be avoided.

The volume of the inside of the container can be increased in action c) such that the flow velocity of the liquid drug in the cannula does not exceed a predetermined rate. The predetermined rate can be selected in at least one embodiment of the method of the present disclosure, such that the flow velocity in the cannula does not exceed about 2 m/s, does not exceed about 1.4 m/s, does not exceed about 1.0 m/s or does not exceed about 0.5 m/s. Alternatively or additionally, the increase in the volume of the inside of the container during exemplary action c) can be controlled based upon the Reynolds number of the flow of liquid drug in the cannula. For example, the change in volume can be limited such that the Reynolds number does not exceed a value where the flow transitions from laminar flow to turbulent flow. Moreover, the reduction of the volume of the inside of the container during action b) can be controlled based upon the pressure in the drug reservoir. For example, reduction in volume can be controlled such that the pressure in the drug reservoir does not exceed 2000 mbar, does not exceed 1000 mbar, or does not exceed 500 mbar.

Without being bound to theory, it is believed that the limits on volume change, described above, can reduce the risk of foam formation and/or bubble formation in the liquid drug filled into the container.

When, after performing action d), the volume contained within the container may include liquid drug with trapped gases. In an exemplary action e) the volume contained within the container may be alternately increased and reduced several times to release gases that might be present in the liquid drug.

In one embodiment, at least during actions b) and c), the drug reservoir can be arranged above the container. Accordingly, gravity forces can assist the filling process.

According to the embodiments described herein, actions b) and c) and, where applicable, action e) may be performed by a drive actuator. The drive actuator can be controlled by an electric control, an electronic control or mechanical control. Examples for such drive actuators include electric motors in combination with gears and/or linkage arrangements, hydraulic or pneumatic drive arrangements, spring force driven mechanical actuators, or the like. Alternatively, the actions may be performed manually.

A connector element can provide, in at least one embodiment, a cannula for providing a fluidic connection between the drug reservoir and the container. When performing action a), the drug reservoir and the container can be structurally connected with each other via the connector element. Accordingly, the connector element can contemporaneously provide a mechanical connection and a fluidic connection between the reservoir and the connector. Furthermore, the end of the cannula can be located within a cavity formed in the connector. Thus, the risk of unintentional contact between a cannula end and another object (e.g., a user) can be significantly reduced.

In at least one embodiment of the method of the present disclosure, after performing action d), the connector element can be separated from the drug reservoir and from the container. Accordingly, the embodiments described herein can be provided with disposable connector elements. Without being bound to theory, it is believed that the use of a new connector for each filling process can reduce the risk of contamination of the liquid drug in the liquid drug reservoir and in the container.

According to the embodiments described herein, an apparatus can be used for filling an ampoule with a liquid drug such as, e.g., insulin, from a liquid drug reservoir. In at least one embodiment, the apparatus can be suitable for use with one or more of the methods described herein. An ampoule to be filled can include a container and a displaceable piston arranged therein. The apparatus may include a housing, a piston rod for driving the piston of the ampoule and a drive for driving the piston rod.

The piston rod can in at least one embodiment be moveable relative to the housing along a longitudinal axis of the housing. Further, the piston rod can include a coupling member for coupling the piston rod to the piston of the ampoule such that, in both directions of the longitudinal axis of the piston rod, a positive or a non-positive locking between can be maintained between the piston rod and the piston. Suitable coupling members include, for example, threaded connections, bayonet connections, snap in connections, magnet couplings, frictional connections (e.g., cone shaped frictional connections), or the like.

The drive in at least one embodiment can actuate the piston rod along the longitudinal axis. The drive may be operable to oscillate the piston rod back and forth along the longitudinal axis several times.

In an exemplary embodiment, the apparatus can be configured for fully automated filling. In one embodiment, the apparatus may include a holding member that holds the container of the ampoule such that, at least while the drive is activated, a positive connection and/or a frictional connection is maintained between the container of the ampoule and the housing in both directions of the longitudinal axis.

As is noted above, the ampoule to be filled may include a container and a displaceable piston arranged therein to define a changeable volume. In at least one embodiment, the apparatus may include a housing, a piston rod that couples to the piston of the ampoule, a holding member for holding the container of the ampoule and a drive for actuating the holding member.

The piston rod can in at least one embodiment be fixed within the housing of the apparatus. The piston rod can include a coupling member for coupling the piston rod to the piston of the ampoule such that a positive or a non-positive locking between the piston rod and the piston is maintained in both directions of movement of the piston rod along the longitudinal axis. Suitable coupling members include, for example, threaded connections, bayonet connections, snap in connections, magnet couplings, frictional connections (e.g., a cone), or the like.

The holding member can be moveable relative to the piston rod along the longitudinal axis of the piston rod. Further, the holding member can be adapted for holding the container of the ampoule such that, at least while the drive is activated, a positive and/or a frictional locking between the container of the ampoule and holding member is maintained in both directions of the longitudinal axis of the piston rod there exists.

According to the embodiments described herein, the maximum pressure inside the liquid drug reservoir can be reduced during the filling process of the ampoule. Thus, the risk of a formation of foam and/or air bubbles within the filled container can be reduced. Furthermore, when the liquid drug reservoir is a pen cartridge, the risk of pushing the piston of the pen cartridge out of the cartridge and of spilling the liquid drug contained therein can be reduced.

In some embodiments of the apparatus, the drive can be oscillated such that drive moves back and forth. For example, the drive can oscillate a movable piston rod or a movable holding member that holds the container along said longitudinal axis of the piston rod. In some embodiments, the drive can oscillate at least three times such as, for example, at least five times in one embodiment, at least eight times in another embodiment or at least ten times in yet another embodiment. Accordingly, filling can take place in several small steps and the pressure within the filling system can be kept at a moderate level.

The apparatuses described herein may further include a sensor for detecting a filling level of an ampoule to be filled. Specifically, the sensor can detect a filled ampoule and emit a signal indicative of a filled ampoule such as, for example, acoustical signal, optical signal, electrical signal or a combination thereof. Accordingly, the sensor can provide a signal that controls the drive (i.e., activates or deactivates). Thus, the sensor and the drive can cooperate to automatically fill an ampoule to a specific filling level.

Moreover, the at least one embodiment of the apparatus can be configured such that drive starts at an initial position upon activation and returns to the initial position upon deactivation. For example, upon deactivation of the drive, the movable piston rod can be positioned in the same position relative to the housing in which it had been positioned before the activation of the drive. Similarly, the holding member can be positioned in the same position relative to the housing in which it had been before the activation of the drive means.

In further embodiments, the apparatus can be designed such that the drive starts at the initial position prior to activation. The movable piston rod or the holding member can be positioned at the initial position by the drive. The initial position can be set such that an ampoule has a maximum interior volume with respect to a stroke when the drive is at the initial position and the ampoule is coupled to the piston rod and held by the holding member. Alternatively, the initial position can be set such that an ampoule has, with respect to the stroke, a minimum inside volume when the drive is at the initial position and the ampoule is coupled to the piston rod and held by the holding member. Depending on the total pressure level that is acceptable in the filling system, the one or the other alternative might be more preferable.

Furthermore, the drive can be configured such that the back and forth movement of a stroke of the drive are substantially identical, i.e., during a single stroke, the amount of reduction of the changeable volume of the container can be about equal to the amount of increase. Accordingly, the drive can cause relative motion between the piston rod and the container. Specifically, the drive can actuate the movable piston rod or the moveable holding member along a stroke having substantially identical back and forth movement. Accordingly, the pressure inside the filling system can be increased step wise, which could mitigate spilling of liquid drug contained within reservoirs such as pen cartridges.

In some embodiments, the drive can be designed such that different portions of a stroke are performed at different speeds. For example, the forth movement of the movable piston rod or the movable holding member can be actuated more rapidly than the back movement of the same stroke. Although the type of liquid drug, the type of container and the dimensions of the filling system may impact filling speed, a more rapid forth movement may shorten filling time. Alternatively, the back movement of the movable piston rod or the movable holding member can be actuated more rapidly than the forth movement of the same stroke. Although the type of liquid drug, the type of container to be filled and the dimensions of the filling system may impact foam or bubble formation, a more rapid back movement may reduce the risk of foam or bubble formation.

Moreover, the drive can be designed such that the speed of the back movement of the drive is substantially constant. Accordingly, the movable piston rod the movable holding member can be moved in the back direction at a substantially constant speed. The substantially constant speed in the back direction can mitigate undesired peaks in the flow velocity of the flow of liquid drug from the liquid drug reservoir to the ampoule, which may be desirable if the fluidic connection is established by a cannula.

According to the embodiments described herein, the drive may comprise a drive actuator that is controlled by electric controls, electronic controls or mechanical controls. The drive actuator can be any suitable actuator such as, for example, electric motors in combination with gears and/or linkage arrangements, hydraulic or pneumatic drive arrangements, spring force driven mechanical actuators, or the like.

Embodiments of the present disclosure further relate to systems for extracting a liquid drug, such as e.g. insulin, from a drug reservoir. In some embodiments, the systems are suitable for use in the methods described herein. The systems may include one or more of the apparatuses described herein and an ampoule comprising a container with a displaceable piston arranged therein. The ampoule can be coupled by the displaceable piston to the coupling member of the piston rod. The ampoule can be held or be held and moved by the holding member that holds the container. With such a system, ampoules can be filled with a liquid drug from a liquid drug reservoir in a convenient manner.

In at least one embodiment of the present disclosure, the ampoule and the drive can be operably coupled such that the drive reduces the interior volume of the ampoule by displacing the movable piston rod or the movable holding member in a forth motion. In some embodiments, the drive can be configured to reduce the volume of the inside of the ampoule with the stroke of the forth movement drive by less than about one half of the maximum volume of the inside of the ampoule, by less than about one fourth of the maximum volume of the inside of the ampoule, or by less than one tenth of the maximum volume of the inside of the ampoule in various embodiments. Accordingly, the container can be filled with several small filling steps and the maximum pressure in the filling system is kept low compared to systems that decrease greater amounts of the maximum volume inside the ampoule. The pressure in the liquid drug reservoir can be kept below critical values for pen cartridges and, when the ampoule and the liquid drug reservoir are fluidically interconnected via a cannula, foam and air bubble formation can be mitigated within the liquid drug that is filled into the container.

Exemplary embodiments of the system may further comprise a drug reservoir containing a liquid drug and a connector with a cannula for fluidically connecting the inside of the ampoule with the inside of the liquid drug reservoir for transferring liquid drug from the drug reservoir to the ampoule.

The systems described herein can be designed such that the maximum flow velocity of the liquid drug is controlled. For example, the drug reservoir, the connector and the drive of the apparatus may be designed such that, when the drive is activated, the maximum flow velocity of the flow of liquid drug in the cannula does not exceed a predetermined rate. In an exemplary embodiment the predetermined rate can be about 2.0 m/s, about 1.4 m/s, about 1.0 m/s, or about 0.5 m/s.

Alternatively, or additionally, the systems can be designed such that the Reynolds number of the flow of the liquid drug is controlled. For example, the ampoule, the drug reservoir, the connector and the drive of the apparatus may be designed such that, when the drive is activated, the Reynolds number of the flow of liquid drug in the cannula does not exceed a value that indicates the flow has transitioned from laminar flow to turbulent flow.

Moreover, the systems can be designed such that the maximum pressure in the drug reservoir is controlled. For example, in at least one embodiment of the system, the ampoule, the drug reservoir, the connector and the drive of the apparatus may be designed such that, when the drive is activated, the maximum pressure in the drug reservoir does not exceed a predetermined pressure. The predetermined pressure can be about 2000 mbar, about 1000 mbar, or about 500 mbar.

Accordingly, the risk of formation of foam and bubbles in the liquid drug that is filled into the ampoule can be reduced.

In some embodiments, the apparatus of the system may further comprise a sensor for detecting the state of the connection between the drug reservoir and the ampoule. Accordingly, the sensor can detect when the drug reservoir and the ampoule are disconnected from each other after a transfer of liquid drug from the drug reservoir to the ampoule. Thus, while the ampoule is still coupled to the piston rod and, where applicable, is still held by the holding member the drive can be activated to remove any gas present in the liquid drug contained in the ampoule. Specifically, the drive can actuate the piston rod or the holding member back and forth several times.

Figure 2:
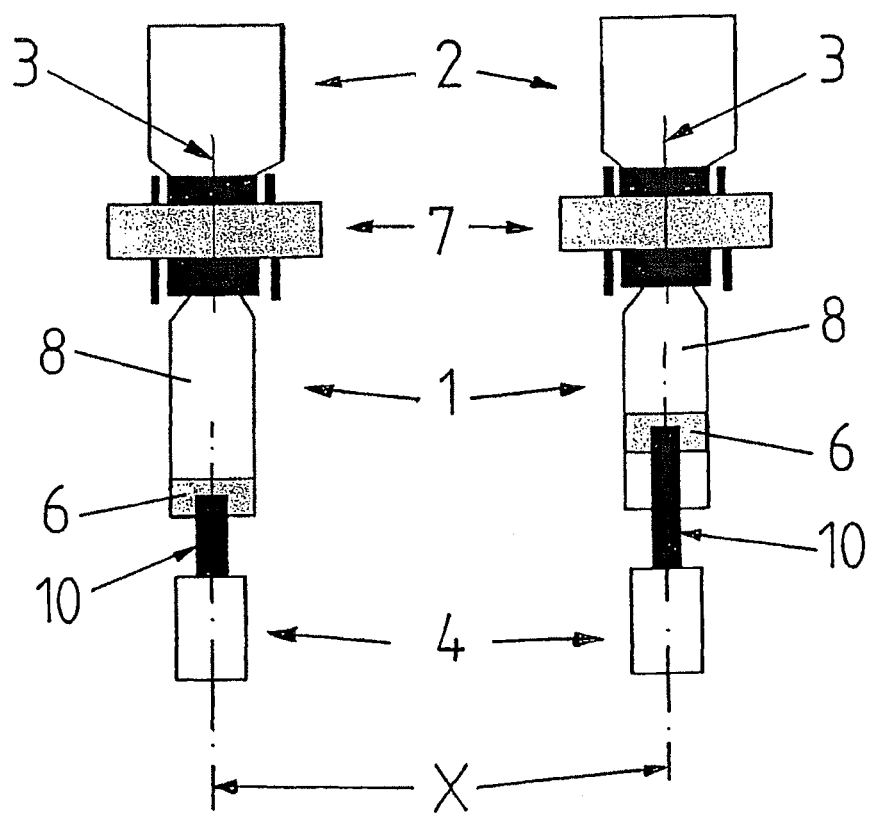
FIGS. 2a and 2b each schematically depict an arrangement for performing methods according to one or more embodiments shown and described herein.
Figure 5A:
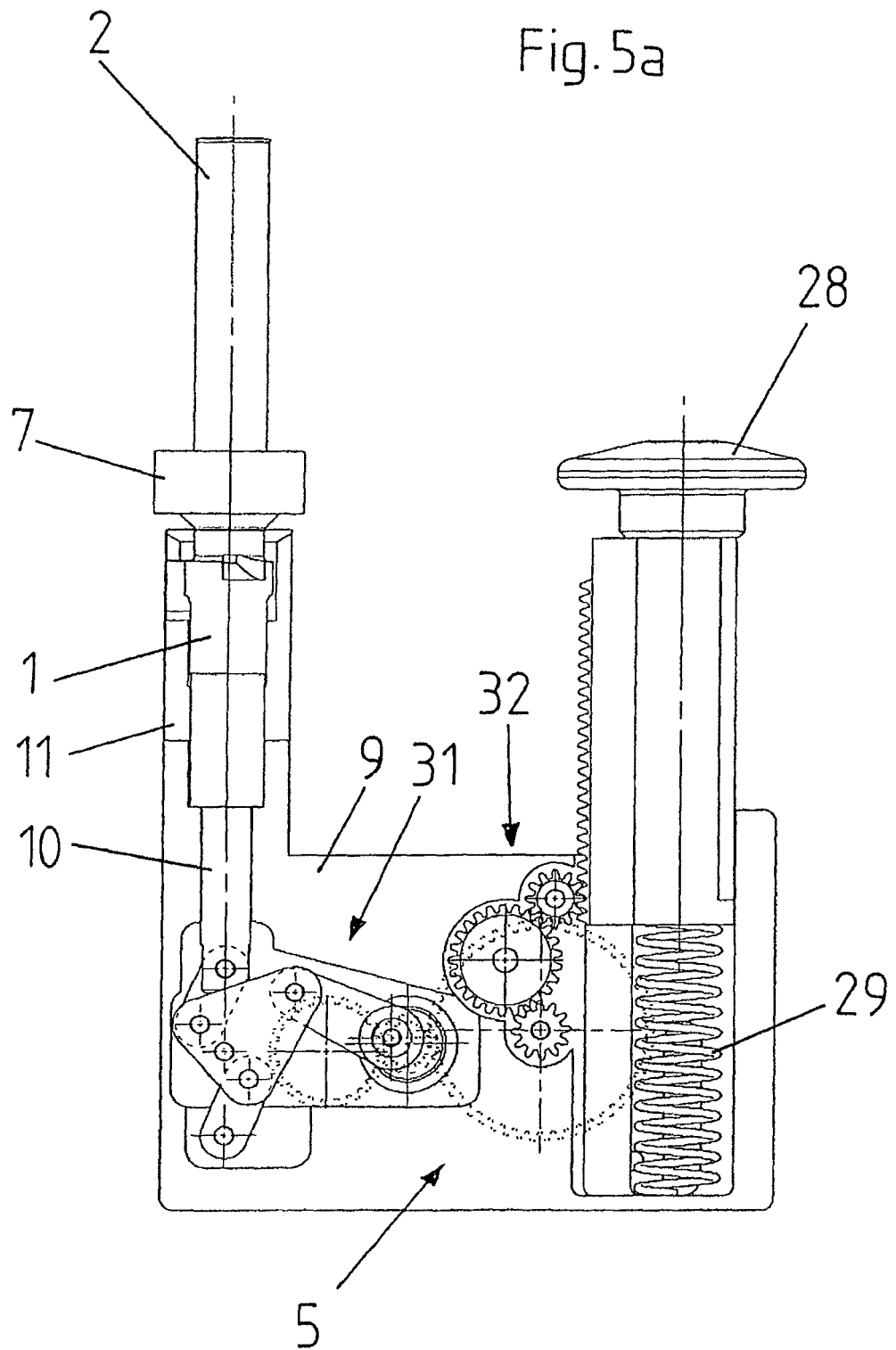
FIGS. 5a and 5b schematically depict an apparatus according to one or more embodiments shown and described herein.
Figure 5B:
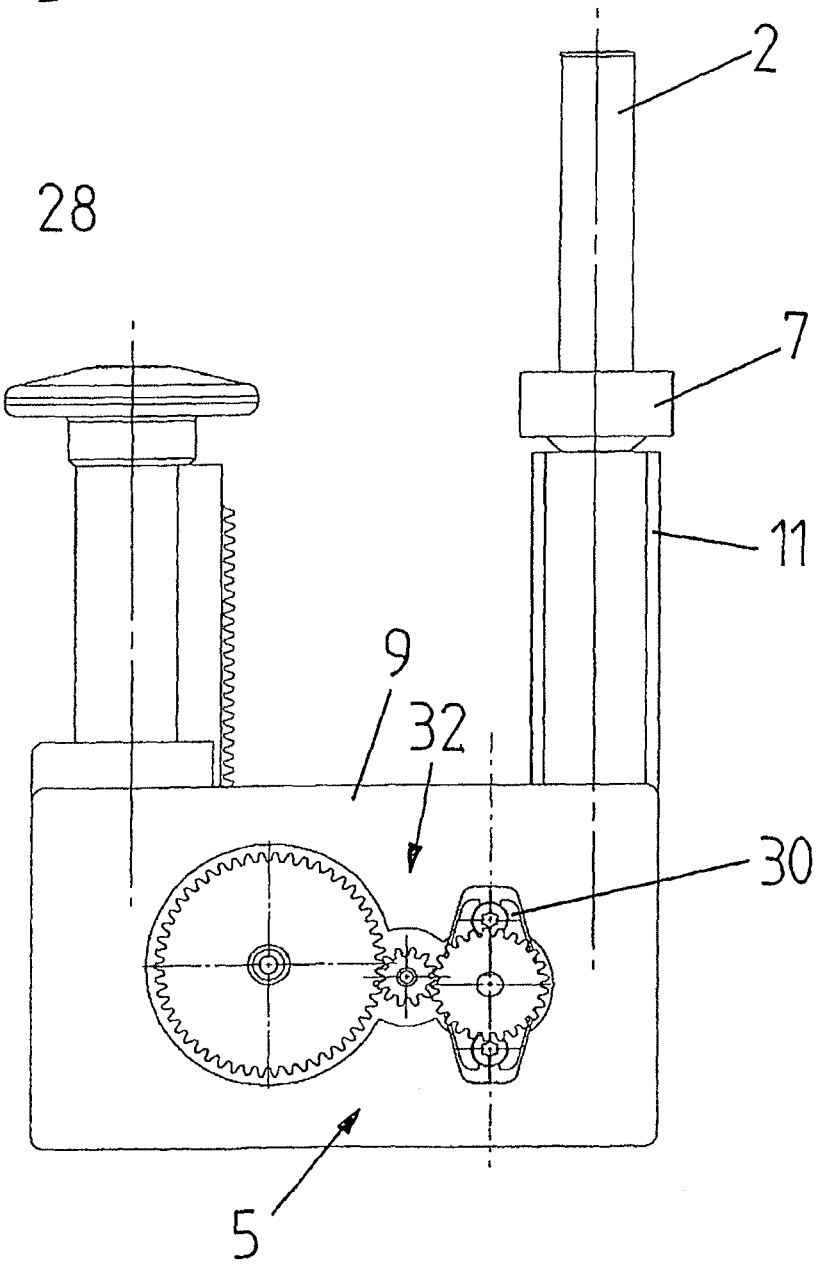

Referring now to FIG. 1, a side view of an exemplary embodiment of an ampoule system is schematically depicted. The system of FIG. 1 comprises a single use ampoule 1 that can be made of plastic. The ampoule 1 can be formed by a container 8 and a piston (not depicted in FIG. 1) arranged therein in displaceable manner. At the backside of the ampoule 1, a multi-use piston rod 10 is coupled to the piston by a threaded connection. At its front face, the ampoule 1 is coupled by a connector 7 with a drug reservoir 2 containing a liquid drug, such as insulin, such that the interior of the ampoule 1 and of the drug reservoir 2 fluidically communicate with each other via a cannula 3 (see FIG. 2) provided by the connector 7. The connector 7 can contemporaneously structurally connect the ampoule 1 and the drug reservoir 2 with each other. As depicted FIG. 1, the liquid drug reservoir 2 can be provided as a vial. It is noted that other embodiments the liquid drug reservoir 2 may be provided, such as a pen cartridge (FIGS. 5a and 5b). In still other embodiments, the drug reservoir 2 may be any device suitable for holding a liquid drug and communicating fluidically with the ampoule 1 via the connector 7. As the use of the ampoule system is described hereinabove, for purposes of brevity, similar details are not repeated hereafter.

Referring now to FIGS. 2a and 2b, an arrangement for performing the embodiments described herein is schematically depicted. The arrangements comprise an ampoule 1, which is formed by a container 8. A piston 6 can be arranged within the container 8 and be displaceable therein. The piston 6 can be coupled via a piston rod 10 with a drive actuator 4. The drive actuator 4 can be electrically powered and operably coupled to the piston rod 10 and the piston 6. The drive actuator 4 can alternately move the piston rod 10 and the piston 6 forward and backward along the longitudinal axis X of the piston rod 10. Accordingly, the inside volume of the ampoule 1 can be alternately reduced and increased. At its front face, the ampoule 1 can be both mechanically coupled and fluidically coupled with a liquid drug reservoir 2, such as e.g. containing insulin, via a connector 7. The connector 7 can comprise a cannula 3 for establishing the fluidic connection between the inside of the ampoule 1 and the inside of the reservoir 2. For example, the cannula 3 can pierce the septums (not depicted) at the front faces of the ampoule 1 and of the reservoir 2.

In some embodiments of the methods described herein, the drive actuator 4 can oscillate several times back and forth and move the piston 6 and the piston rod 10 between the fully retracted position (FIG. 2*a*) and the partially pushed in position shown in (FIG. 2*b*).

Figure 3:
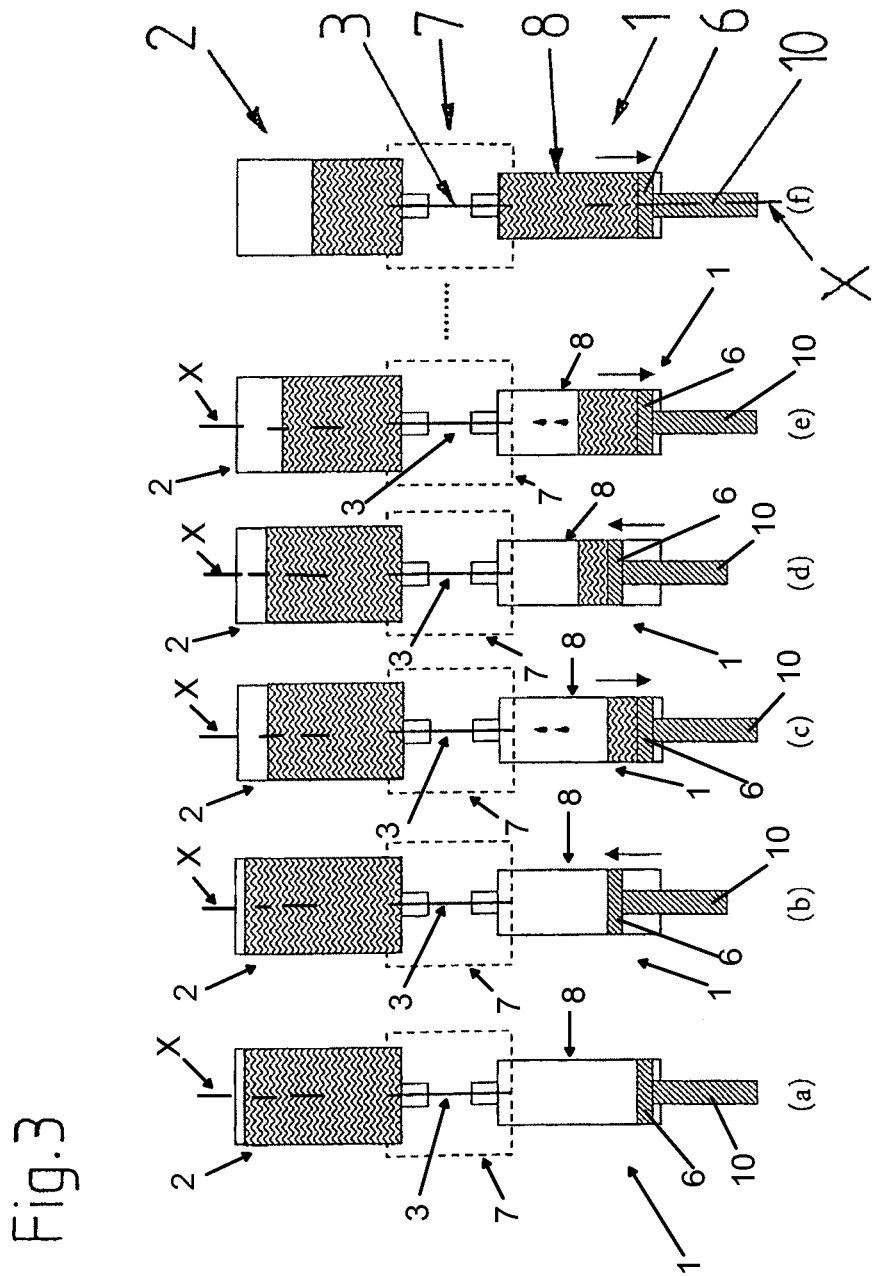
FIG. 3 schematically depicts a method according to one or more embodiments shown and described herein.

Referring now to FIG. 3, an exemplary filling process is schematically depicted from the left to the right. Various situations (a) to (f) can be encountered during the course of filling the ampoule 1. Beginning with situation (a), which corresponds to the fully retracted position of FIG. 2*a*, the ampoule 1 can be empty. The piston 6 can be moved forth and back (situations (b) to (e)) several times. Accordingly, the ampoule 1 can be stepwise filled with insulin from the reservoir 2, until it is substantially filled as depicted in situation (f).

Figure 4B:
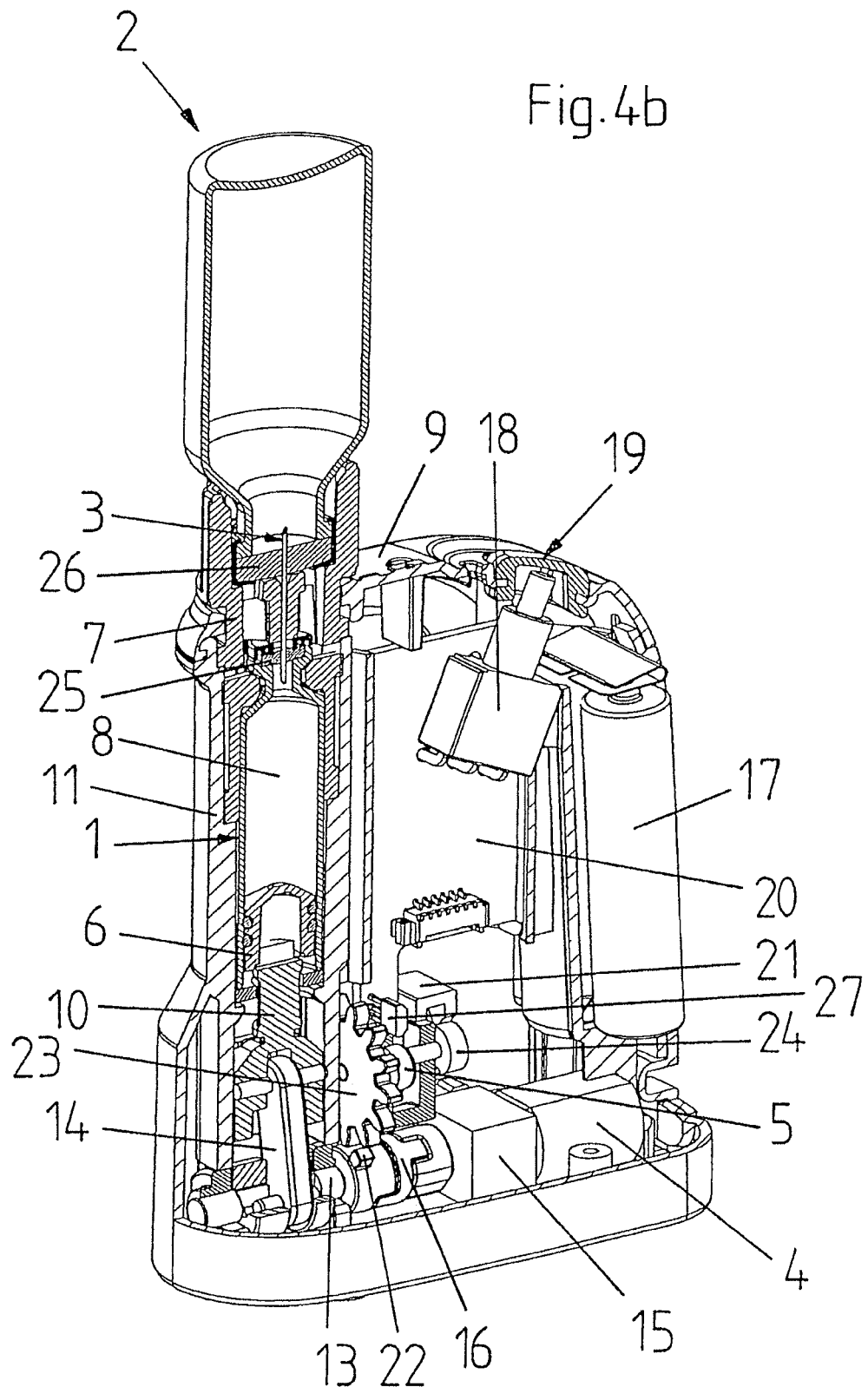

Referring collectively to FIGS. 4*a* to 4*c*, an embodiment of an apparatus of the present disclosure is schematically depicted. FIG. 4*a* schematically depicts an embodiment of the apparatus, FIG. 4*b* schematically depicts an embodiment of the apparatus in use and FIG. 4*c* schematically depicts the drive arrangement of an embodiment of the apparatus.

In one embodiment the apparatus comprises a housing 9 having a cavity 12 for receiving the ampoule 1 to be filled. A piston rod 10 can be located at the bottom of the cavity 12. The piston rod 10 can be moved up and down by a crank mechanism. The crank mechanism is formed by a crankshaft 13 and a connecting rod 14, which can be moved by an electric drive unit. The electric drive unit comprises the drive actuator 4 provided e.g., as an electric motor. The drive actuator 4 can be operably coupled with a gearbox 15. The gearbox 15 can be rotatably connected to the crankshaft 13 via an Oldham-coupling 16. The drive unit furthermore comprises two batteries 17 for providing the electric energy for the drive actuator 4 and an electric or electronic control system for controlling the drive actuator 4. The control system can comprise an activating switch 18 which can be actuated by pressing a button 19 at the outside of the housing 9 and a mechanical counting switch 21. The mechanical counting switch 21 can be actuated at a predetermined number of revolutions (e.g., about every thirteen) of the crankshaft 13 by a counting gear arrangement. The counting arrangement can formed by a pusher dog 22 on the Oldham-coupling which drives a counting pinion 23 which in turn rotates a cam disk 24 that actuates the mechanical counting switch 21. Instead of, or in addition to, the mechanical counting switch 21, the counting arrangement can comprise a sensor 27 with a printed circuit board 20. Specifically, the sensor 27 can be triggered once a magnetic element 5 is positioned in front of it.

Referring now to FIG. 4*b*, the ampoule 1 to be filled can comprise a container 8 (body) and a piston 6 arranged therein in a displaceable manner. The ampoule 1 can be inserted into the cavity 12 (FIG. 4*a*) in the housing and be radially guided by the boundary walls 11 of the cavity 12. When the ampoule 1 is introduced into the cavity 12, the piston 6 of the ampoule can be coupled to the piston rod 10 of the apparatus by rotating the ampoule 1 when the ampoule 1 has reached the bottom of the cavity 12. Accordingly, a bayonet joint can be established between corresponding bayonet joint mating halves formed by the piston 6 and the piston rod 10. After the bayonet joint is established, a connector 7 with a cannula 3 can be mounted to the opening of the cavity 12 by a bayonet joint and axially securing the ampoule 1 in the cavity 12 by positively locking it between the bottom of the cavity 12 and the connector 7. The cannula 3 can penetrate a septum 25 arranged at the front face of the ampoule 1. The reservoir 2 containing insulin can then be pushed top down into a receiving cavity of the connector 7. The cannula 3 can pierce a septum 26 of the reservoir 2 with the other end of the cannula 3. Thus, a fluidic connection can be established between the inner spaces of the ampoule 1 and the reservoir 2.

Referring collectively to FIGS. 4*a* to 4*c*, in order to achieve a maximum filling of the ampoule 1, at the start of the filling operation, the piston 6 of the ampoule 1 is positioned in the fully retracted position. The filling operation can be started by pressing the button 19, which in turn actuates the activating switch 18. Now the batteries 17 supply electrical energy to the drive actuator 4, which via the gearbox 15, the Oldham-coupling 16 and the crankshaft 13, drives the connecting rod 14. The connecting rod 14 is pivotably connected with the piston rod 10 such that a stroke movement of the piston rod 10 results, i.e. the rotation of the axis of the drive actuator 4 is transformed into translational (linear) movement of the piston rod 10 and the connected piston 6 along the longitudinal axis X. Each upward movement of the piston 6 displaces some air from the ampoule 1 into the reservoir 2, and each downward movement of the piston 6 displaces some insulin from the reservoir 2 into the ampoule 1. The number of strokes needed to fill the ampoule 1 is determined mainly by the ratio of the stroke to the length of the ampoule 1. Accordingly, the operating principle can be followed to avoid an overfilling of the ampoule 1. For example, in at least one embodiment about 10 to about 15 strokes can be sufficient for completely filling the ampoule 1. The piston 6 can be returned to the fully retracted position at the end of the filling process to achieve a maximum filling volume. This can be ensured by the counting switches in combination with the counting gear arrangement described above in greater detail. For every complete stroke of the piston 6, the Oldham coupling 16 is rotated a full revolution (360°) so that the pusher dog 22 arranged thereon rotates the counting pinion 23 further by one tooth. After a full revolution of the counting pinion 23, the cam disk 24 actuates the mechanical counting switch 21. Alternatively the magnetic element 5 can triggers the sensor 27 with the printed circuit board 20, which in turn stops the filling process. The number of teeth in this construction determines the number of strokes that are performed during one filling process. After the filling process has been stopped, the reservoir 2 and the ampoule 1 can be removed with the connector 7 out of the cavity 12.

Referring collectively to FIGS. 5*a* and 5*b*, another embodiment of an apparatus is schematically depicted. This embodiment of the apparatus differs from the embodiment of the apparatus described above with reference to FIGS. 4*a* to 4*c* mainly in that it comprises a mechanical drive unit instead of an electrical drive unit. The interconnection between the piston rod 10 and the piston (not depicted in FIGS. 5*a* and 5*b*) of the ampoule 1 as well as between the ampoule 1 and the reservoir 2 via the connector 7 is established in a substantially similar manner as the embodiment described above with reference to FIGS. 4*a* to 4*c*. However, in the present embodiment, the reservoir 2 is not formed by a vial, but as a pen cartridge, which, e.g., contains insulin.

In at least one embodiment of the apparatus, actuating button 28 can be pushed down to put a spring 29 under compressive stress. A mechanism can be utilized allow the actuating button 28 to be pushed down without starting the filling process. For example, the filling process can be started once the spring 29 has been compressed to a certain level (e.g., a maximum compressive stress). The energy stored in the spring 29 can then be transmitted to the piston of the ampoule 1 in a controlled manner. One difference between using such a mechanical drive unit instead of an electric drive unit involves controlling the spring 29 during its energy delivery. A viscous damping element 30 (rotary damper) can be utilized to control the spring. The viscous damping element 30 can ensure that the energy of the spring 29 is transmitted, with the correct pace, to a knee lever arrangement 31. The knee lever arrangement 31 transforms a rotational force provided from a gear mechanism 32 that is driven by the spring 29 into translational movement. The translation movement drives the piston rod 10 and the piston in the ampoule 1 upward and downward. The apparatus can be designed such that the filling process can be started with only one actuation of the actuating button 28. The filling process is complete once the spring 29 is relaxed and thus no longer supplies energy to the filling mechanism. The upward and downward movement of the piston can fill the ampoule 1 as is described in greater detail hereinabove.

Figure 6A:
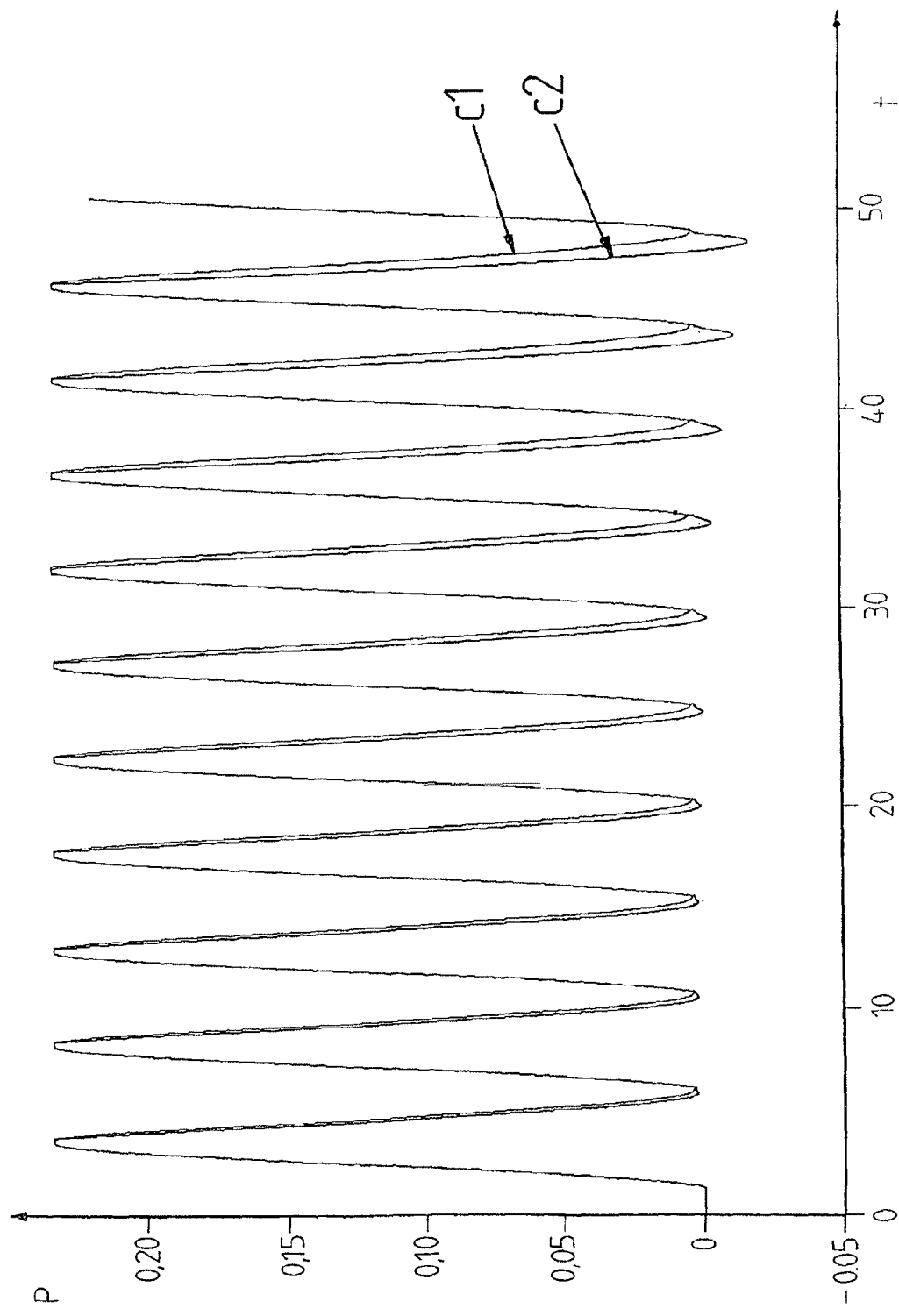
FIG. 6a graphically depicts system pressures and the Reynolds number in the cannula during performance of methods according to one or more embodiments shown and described herein using an embodiment of the apparatus schematically depicted in FIGS. 4a to 4c.

FIG. 6a graphically depicts an exemplary indication of the pressure P in units of bar inside the reservoir 2 and inside the ampoule 1 over the time t in units of seconds during performance of a method according to the embodiments described herein with an embodiment of the apparatus depicted in FIGS. 5a and 5b. FIG. 6a graphically depicts the Reynolds number Re of the flow of insulin in the cannula over the time t in units of seconds during performance of a method according to the embodiments described herein with an embodiment of the apparatus depicted in FIGS. 5a and 5b.

Referring now to FIG. 6a, the pressure c1 inside the drug reservoir 2, which can be a reservoir for insulin, and the pressure c2 inside the ampoule 1 are graphically depicted. During each forward movement of the piston in the ampoule 1, which displaces air from the ampoule 1 into the drug reservoir 2, the pressure c1 and the pressure c2 are increased from about 0.00 bar to about 0.25 bar. During the subsequent downward movement of the piston, which displaces insulin from the drug reservoir 2 via the cannula into the ampoule 1, the pressure c1 and pressure c2 fall back to about 0.00 bar. However, with an increase of the number of strokes performed (generally indicated by the number of periods) the pressure c2 inside the ampoule 1 increasingly falls slightly below 0.00 bar, as a result of the decreasing volume of air inside the ampoule 1.

Referring now to FIG. 6b, the maximum Reynolds number Re of the flow of insulin in the cannula during a single stroke (i.e., one forward and backward movement) increases as the total number of strokes increases. Specifically, the maximum Reynolds number Re increases from about 200 during the first stroke to about 700 during the last stroke, which is a result of the pressure c2 (FIG. 6a) in the ampoule 1 increasingly falling slightly below 0.00 bar.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

While various embodiments of the systems, methods, and apparatus of the present disclosure have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

What is claimed is:

1. A method of automatically filling a container with a liquid drug from a drug reservoir, the method comprising:
   a) connecting a container and a drug reservoir with a cannula such that the drug reservoir and the container fluidically communicate with each other via the cannula, while being hermetically sealed;
   b) reducing a first volume contained within the container to displace a gaseous medium from the first volume of the container via the cannula into a second volume contained within the drug reservoir by activating a drive coupled to the container;
   c) increasing the first volume of the container to displace liquid drug from the second volume of the drug reservoir into the first volume of the container to fill the container; and
   d) disconnecting the container and the drug reservoir, wherein action b) and action c) are successively performed more than once to stepwise increase an amount of liquid drug displaced to the first volume of the container; and
   wherein: action b) and action c) are successively performed more than once before performing action d) to reduce the risk of formation of foam and/or air bubbles within the liquid drug that is filled into the container; and during each performance of b) and c) the drug reservoir is arranged above the container;
   wherein action (d) is performed after sensing a fill level with a sensor directly attached to and linearly extending out from a circuit board, the sensor coupled to the drive and after sending of a signal by the sensor to the drive to deactivate the drive, the sensor is triggered to deactivate the drive once a magnetic element coupled to the drive is positioned in front of the sensor and between the sensor and a pinion; and
   wherein actions b) and c) comprise movement of a piston rod moving a piston displaceable within the container, the magnetic element being coupled to the pinion rotating with each stroke of the piston.

2. The method according to claim 1, wherein the container is a syringe type container, or a bag type container.

3. The method according to claim 1, wherein action b) and action c) are successively performed at least three times.

4. The method according to claim 1, wherein action b) and action c) are successively performed until the first volume of the container is substantially filled with the liquid drug.

5. The method according to claim 1, wherein the first volume of the container has a substantially same size while action d) is performed as the first volume of the container prior to a first instance of action b).

6. The method according to claim 1, wherein action b) is performed before action c) or action c) is performed before action b).

7. The method according to claim 1, wherein the first volume of the container is reduced by less than one half of a maximum volume of the container in action b).

8. The method according to claim 1, wherein an amount of increase in the first volume of the container during action c) is substantially identical to an amount of reduction in the first volume of the container during action b).

9. The method according to claim 1, wherein action b) is performed immediately prior to and more rapidly than action c) or action c) is performed immediately prior to and more rapidly than action b).

10. The method according to claim 1, wherein a speed of increase in the first volume of the container during action c) is substantially constant.

11. The method according to claim 1, wherein during action c) a flow velocity of the liquid drug in the cannula does not exceed about 2 m/s.

12. The method according to claim 1, wherein during action c) the Reynolds number of the liquid drug flowing in the cannula does not exceed a value indicative of a transition from laminar flow to turbulent flow.

13. The method according to claim 1, wherein during action b) pressure in the drug reservoir does not exceed a pressure selected from the group consisting of 2000 mbar, 1000 mbar, and 500 mbar.

14. The method according to claim 1, wherein after action d), the first volume of the container in a further action e) is alternately increased and reduced several times to remove gas from the liquid drug contained in the container.

15. The method according to claim 14, wherein the action b) and action c), and action e) are performed with the drive actuator that is controlled by an electric control, an electronic control, or a mechanical control.

16. The method according to claim 1 wherein at the start of filling the container when empty and at the end of filling the container, the piston is in the same position within the container body.

17. The method according to claim 1, wherein a connector structurally connects the drug reservoir to the container during action a), and the connector comprises the cannula.

18. The method according to claim 17, further comprising, after action d), separating the connector from the drug reservoir; and disposing the connector.

19. The method of claim 1 further comprising a button and an activating switch attached to the circuit board for the activation of the drive.

* * * * *

UNITED STATES PATENT AND TRADEMARK OFFICE
CERTIFICATE OF CORRECTION

PATENT NO. : 9,089,647 B2  
APPLICATION NO. : 13/492008  
DATED : July 28, 2015  
INVENTOR(S) : Roger Haenggi et al.

Page 1 of 2

It is certified that error appears in the above-identified patent and that said Letters Patent is hereby corrected as shown below:

Specification

Col. 1, Line 64,
"the ampoule is filled with air. The ampoule can then be" should be
--the ampoule to be filled with air. The ampoule can then be--;

Col. 2, Line 15,
"dental needle sticks can be reduced compared filling a syringe" should read
--dental needle sticks can be reduced compared to filling a syringe--;

Col. 2, Line 54,
"manner. The piston rod that can be moveable relative to the" should read
--manner. The piston rod can be moveable relative to the--;

Col. 3, Line 2,
"rod that can be fixed with respect to the housing. The piston" should read
--rod can be fixed with respect to the housing. The piston--;

Col. 5, Line 4,
"the container types described herein are suitable for use the" should read
--the container types described herein are suitable for use in the--;

Col. 7, Line 61,
"tions of the longitudinal axis of the piston rod there exists." should read
--tions of the longitudinal axis of the piston rod therein exists.--;

Col. 9, Line 8,
"Accordingly, the movable piston rod the movable holding" should read
--Accordingly, the movable piston rod of the movable holding--;

Signed and Sealed this  
Thirty-first Day of May, 2016

Michelle K. Lee  
*Director of the United States Patent and Trademark Office*

CERTIFICATE OF CORRECTION (continued)

U.S. Pat. No. 9,089,647 B2

Col. 10, Line 47,
"2 can be provided as a vial. It is noted that other embodiments" should read
--2 can be provided as a vial. It is noted that in other embodiments--;

Col. 11, Line 47,
"gear arrangement. The counting arrangement can formed by" should read
--gear arrangement. The counting arrangement can be formed by--;

Col. 12, Line 42,
"Alternatively the magnetic element 5 can triggers the sensor" should read
--Alternatively the magnetic element 5 can trigger the sensor--;

Col. 12, Line 64,
"compressive stress. A mechanism can be utilized allow the" should read
--compressive stress. A mechanism can be utilized allowing the--;

Col. 13, Line 12,
"29 into translational movement. The translation movement" should read
--29 into translational movement. The translational movement--; and

Claims

Col. 14, Claim 1, Line 47,
"wherein action (d) is performed after sensing a fill level" should read
--wherein action d) is performed after sensing a fill level--.